United States Patent [19]
Parker et al.

[11] Patent Number: 6,013,520
[45] Date of Patent: Jan. 11, 2000

[54] BREAST TUMOR CELLS FOR STUDY OF NONIONIZING RADIATION EFFECTS

[75] Inventors: Jill E. Parker, Floresville; Johnathan L. Kiel, Universal City, both of Tex.

[73] Assignee: The United States of America as represented by the Secretary of the Air Force, Washington, D.C.

[21] Appl. No.: 09/140,069

[22] Filed: Aug. 20, 1998

[51] Int. Cl.$^7$ ..................................................... C12N 5/10
[52] U.S. Cl. .............................................................. 435/354
[58] Field of Search ...................................... 435/325, 354

[56] References Cited

U.S. PATENT DOCUMENTS 5,464,768  11/1995  Kiel et al. ................................ 435/325

OTHER PUBLICATIONS

American Type Culture Collection (ATCC) ltr dated May 20, 1994, acknowledging receipt of materials designated 69617 and 69618.

American Type Culture Collection (ATCC) ltr dated Sep. 13, 1997, acknowledging receipt of materials designated CRL–12184 and CRL–12185.

J.G. Bruno, J.L. Kiel, Effect of Radio–Frequency Radiation (RFR) and Diazoluminomelanin (DALM) on the Growth Potential of Bacilli, Electricity and Magnetism in Biology and Medicine, Martin Blank, Ed., San Francisco Press, Inc., ©1993, no month given.

J.L. Kiel, J.E. Parker, J.L. Alls, S.B. Pruett, The Cellular Stress Transponder: Mediator of Electromagentic Effects or Artifacts?, Nanobiology (1992, no month given) 1, 491–503.

J.G. Bruno, J.L. Kiel, Synthesis of Diazoluminomelanin (DALM) in HL–60 Cells for Possible Ues as a Cellular––Level Microwave Dosimeter, Bioelectromagnetics 15:315–328 (1994, no month given).

I.J. Amber, J.B. Hibbs, R.R. Taintor, Z. Vavrin, The L–Arginine Dependent Effector Mechanism Is Induced in Murine Adenocarcinoma Cells by Culture Supernatant From Cytotoxic Activated Microphages, J. of Leukocyte Biology 43:187–192 (1988, no month given).

J.G. Bruno, J.E. Parker, J.L. Kiel, Plant Nitrate Reductase Gene Fragments Enhance Nitrite Production in Activated Murine Macrophage Cell Lines, Biochemical and Biophysical Research Communications, vol. 201, No. 1, 1994(no month given), pp. 284–289.

*Primary Examiner*—James Ketter
*Attorney, Agent, or Firm*—Charles E. Bricker; Thomas L. Kundert

[57] ABSTRACT

The cell line EMT-6 are transformed with the chromosomal insertion of the plasmid $pSV_2neoNR10_1$, ATCC No. 69617. The transformed cells, $EMT-6/pSV_2neoNR10_1$, produce diazoluminomelanin (DALM) intracellularly when provided with nitrate, luminol and 3-amino-L-tyrosine·HCl (3AT). The modified cells can be used to study mechanisms for radiofrequency and light radiation interactions with breast tumor cells in vitro and in mice. The effects of drugs, hormones, and cytokines that affect the expression of nitric oxide synthase and its activity can also be studied to understand the effects of these materials on breast tumor cells.

1 Claim, 3 Drawing Sheets

BREAST TUMOR CELLS FOR STUDY OF NONIONIZING RADIATION EFFECTS

RIGHTS OF THE GOVERNMENT

The invention described herein may be manufactured and used by or for the Government of the United States for all governmental purposes without the payment of any royalty.

BACKGROUND OF THE INVENTION

The present invention relates to murine mammary carcinoma cells modified with a nitrate reductase gene fragment.

One of the most pressing health issues today is breast cancer. In the industrial world, about one woman in every nine can expect to develop breast cancer in her lifetime. In the United States, it is the most common cancer amongst women, with an annual incidence of about 175,000 new cases and nearly 50,000 deaths.

Despite an ongoing improvement in our understanding of the disease, breast cancer has remained resistant to medical intervention. Most clinical initiatives are focused on early diagnosis, followed by conventional forms of intervention, particularly surgery and chemotherapy. Such interventions are of limited success, particularly in patients where the tumor has undergone metastasis. There is a pressing need to improve the arsenal of therapies available to provide more precise and more effective treatment in a less invasive way.

Aside from the ethical issues of testing therapies on their persons, human subjects are too expensive to feed and house, and are too unpredictable in their behavior. Consequently, most therapys are tested in vitro or in vivo, using laboratory test subjects such as mice and rats. One major problem with in vivo tests is that the test subject must generally be euthanized in order to determine the effect of the therapy.

We have modified EMT-6 cells (spontaneous Balb/c mammary adenocarcinoma cell line) in such manner that the modified cells can be used to study mechanisms for radiofrequency and light radiation interactions with breast tumor cells in vitro and in mice. The effects of drugs, hormones, and cytokines that affect the expression of nitric oxide synthase and its activity can also be studied to understand the effects of these materials on breast tumor cells.

Accordingly, it is an object of the present invention to provide murine mammary carcinoma cells modified with a nitrate reductase gene fragment.

Other objects, aspects and advantages of the present invention will be apparent to those skilled in the art from a reading of the following detailed disclosure of the invention.

SUMMARY OF THE INVENTION

In accordance with the present invention there are provided EMT-6 cells transformed with the chromosomal insertion of the plasmid $pSV_2neoNR10_1$, ATCC No. 69617. The transformed cells, hereinafter referred to as EMT-6/$pSV_2neoNR10_1$, produce diazoluminomelanin (DALM) intracellularly when provided with nitrate, luminol and 3-amino-L-tyrosine·HCl (3AT).

DETAILED DESCRIPTION OF THE INVENTION

The EMT-6 parent cell line was obtained from Dr. John Hibbs, VA Medical Center, Salt Lake City, Utah.

EMT-6 cells were transfected with the $pSV_2neoNR10_1$ plasmid using the technique described in Kiel et al, U.S. Pat. No. 5,464,768. The $pSV_2neoNR10_1$ plasmid is the neomycin resistant plasmid $pSV_2neo$ modified by insertion of the 1.1 kb base pair barley nitrate reductase (NR) gene fragment between the EcoR1 sites. As a control, the $pSV_2neo$ plasmid, without the barley nitrate reductase gene fragment, was introduced into this cell line. The transfectants were selected for by using 500 micrograms/ml of the antibiotic geneticin (neomycin) in the growth medium. Two active clones were isolated in addition to the control clone. The two new clones were designated EMT-6-1.1(1) and EMT-6-I.1(2). The control clone was designated EMT-6-NEO. The cells were grown in RPMI 1640 medium without phenol red, containing 39 mM nitrate, 0.5 mg/10 ml luminol and 0.149 mM 3-amino-L-tyrosine·HCl (3AT), designated 1X3AT medium. When the luminol and 3AT concentrations were 1 mg/10 ml and 0.297 mM, respectively, the medium was designated 2X3AT. Each of these media had 10 U/ml of mouse gamma-interferon and 5 nanograms/ml of *E. coli* endotoxin (LPS) added to them. The clones EMT-6-1.1(1) and EMT-6-I.1(2) have been deposited with the American Type Culture Collection, receiving the ATCC Designations CRL-12184 and CRL-12185, respectively.

The transfected EMT-6 cells produce diazoluminomelanin (DALM) intracellularly when grown in 3AT media, i.e., media containing nitrate, luminol and 3AT. DALM is a luminescent compound having repeating units of the formula:

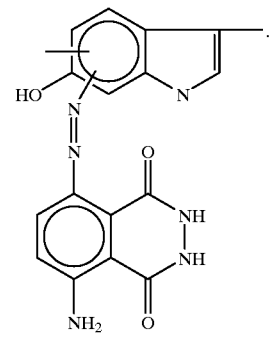

DALM can be used for chemiluminescent immunoassays for biological and chemical agents; in radiofrequency and ionizing radiation dosimeters; and for RNA/DNA hybridization assays for viruses and genetic detection.

Figure 1:
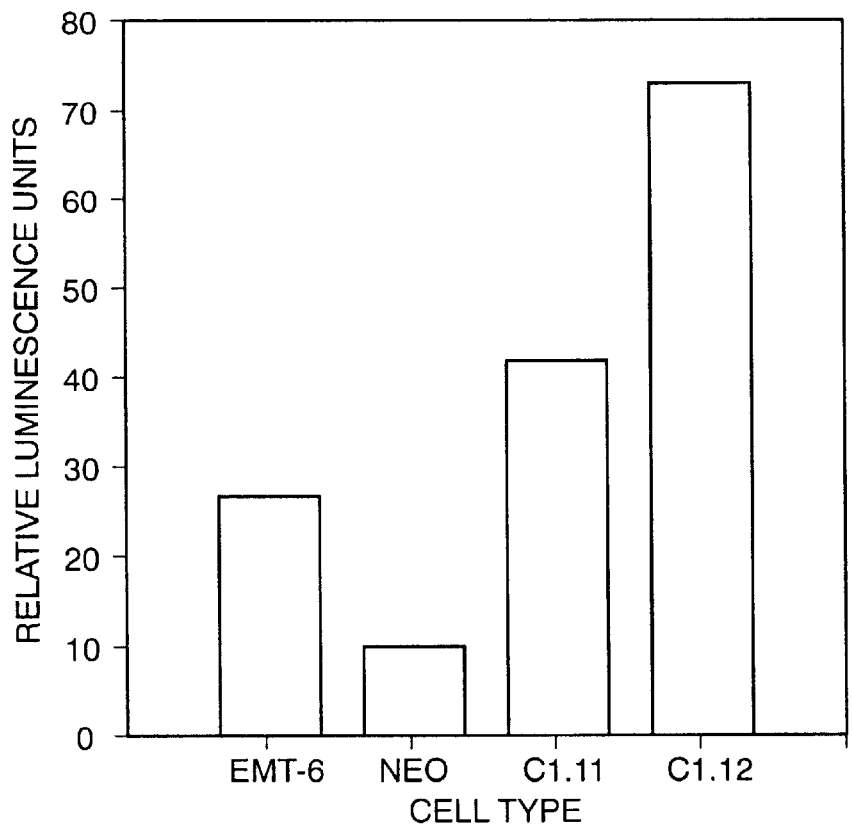
FIG. 1 and FIG. 2 shows the relative thermochemiluminescence (TCL) of transformed cells versus non-transformed cells.
Figure 2:
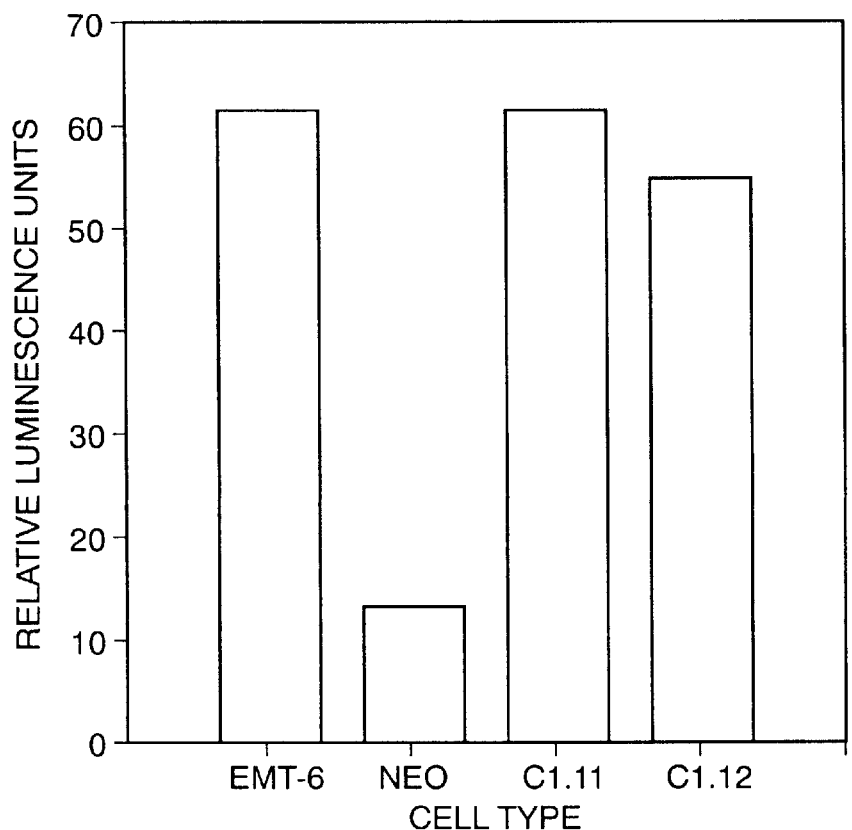

To produce DALM, the cells were grown in one or the other of the aforementioned 3AT media. Referring to the drawings, FIGS. 1 and 2 show the relative thermochemiluminescence (TCL) of each cell type. Each sample of 50 microliters of cell suspension of cells previously washed three times in isotonic phosphate buffered saline and re-suspended in 100 microliters of isotonic phosphate buffered saline, plus 50 microliters of PBS, was activated with 100 microliters 0.3% hydrogen peroxide and 100 microliters of 0.3M sodium bicarbonate solution and heated to 45° C., then counted in a Turner 20e Luminometer (Turner Designs, Mountain View Calif.) for 30 seconds. On the 8th day of culture in 1X3AT medium, the 1.1(2) clone showed the most TCL, followed by 1.1(1), the parent cell line EMT-6, and finally, the NEO control clone. When 2X3AT medium was used for 8 days, the EMT-6, 1.1(1), and 1.1(2) reached a similar maximum TCL. The NEO clone remained relatively low.

Figure 3:
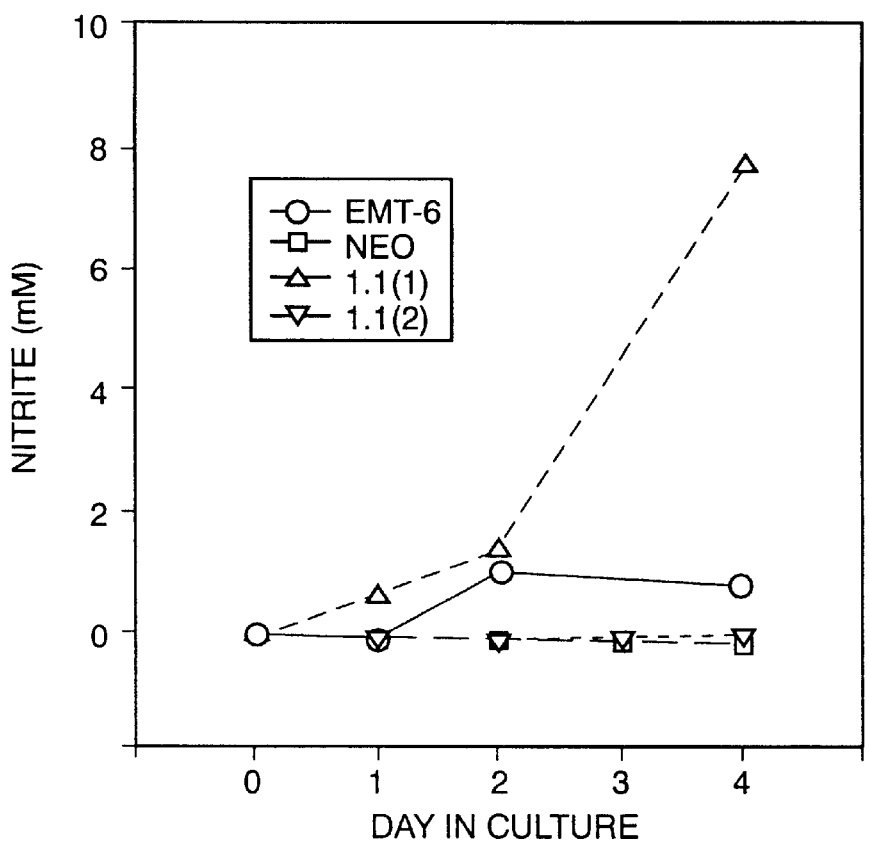
FIG. 3 shows the kinetics of nitrite production by the parent line and various transformed clones.
Figure 4:
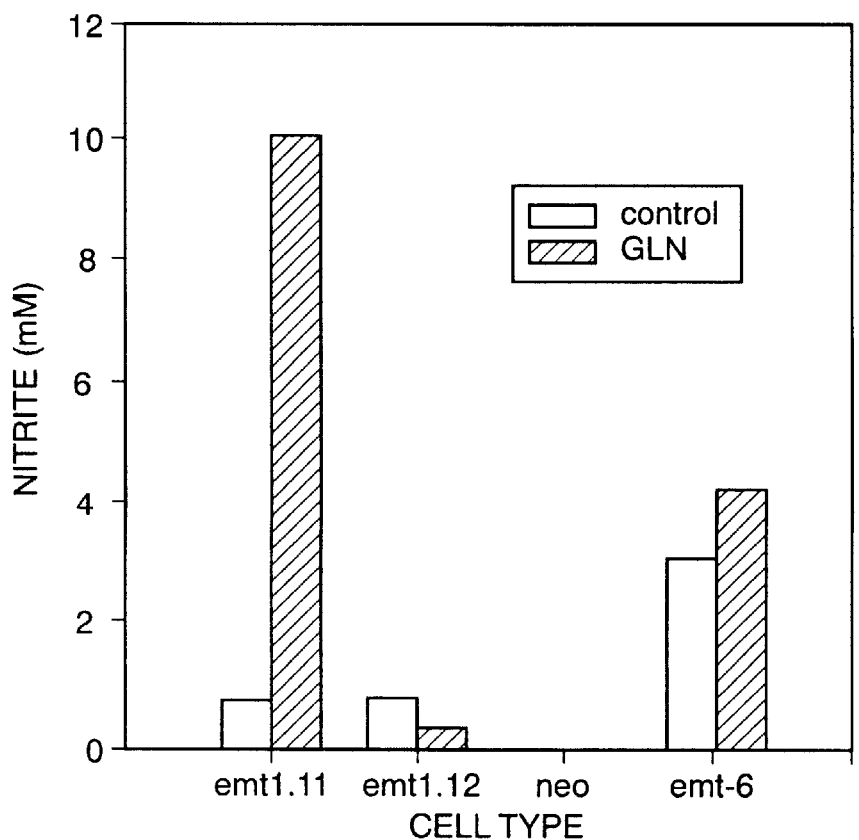
FIGS. 4–6 show the nitrite-production responses of the control, parent, and transfected clones when different time regimens of stimulation are applied.
Figure 5:
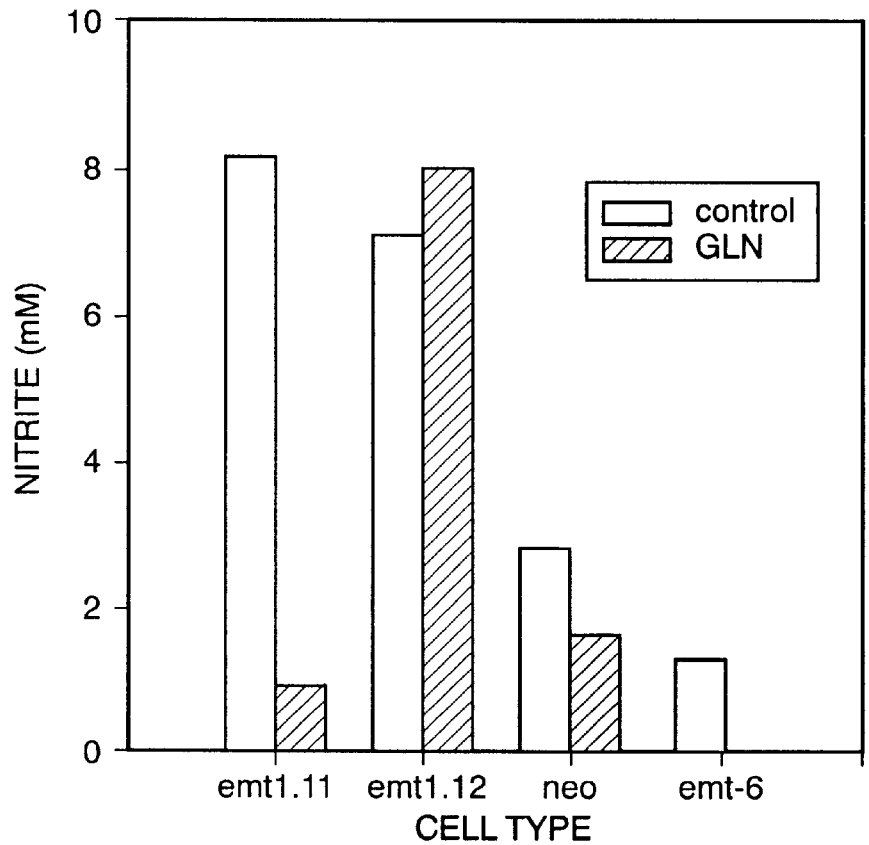
Figure 6:
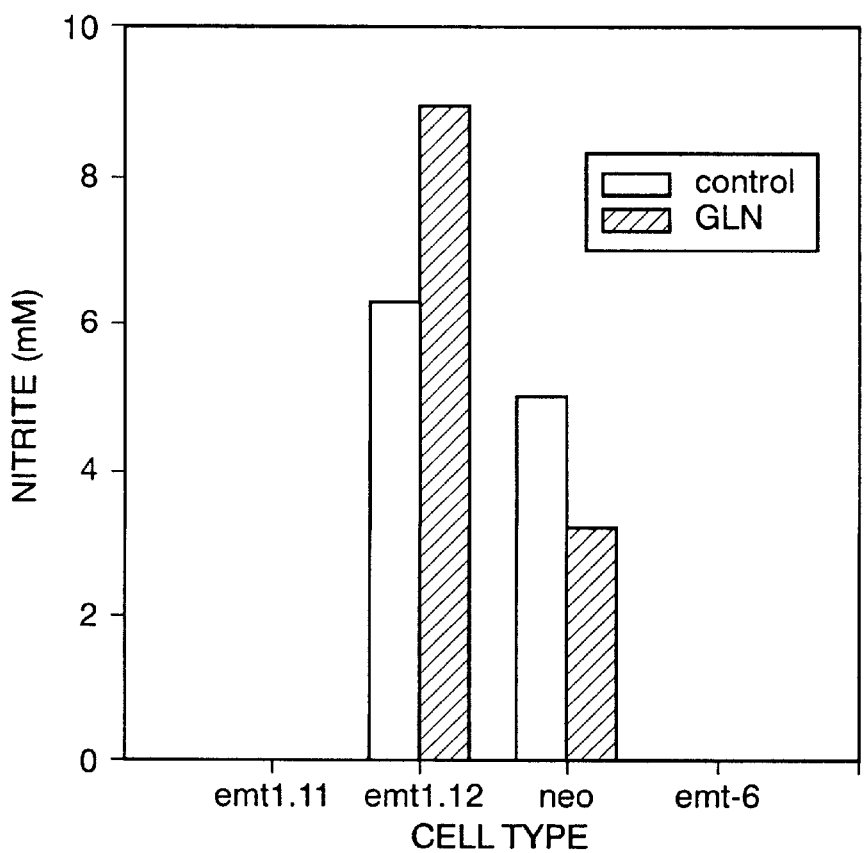

FIG. 3 shows the kinetics of nitrite production by the parent line and various clones. FIGS. 4–6 show the nitrite-production responses of the control, parent, and transfected clones when different time regimens of stimulation are applied. 2,3-Diaminonaphthalene (DAN) and LPS from $E.$ $Coli$ serotype 055:B5 were obtained from Sigma Chemical Company, St. Louis, Mo. Murine INF-γ was obtained from Genzyme, Cambridge Mass. A stock solution of DAN (0.065 mg/ml) was prepared in 0.62M HCl. Stock solutions of LPS and INF-γ were prepared in RPMI 1640 medium.

Cells were plated in T-75 flasks and activated by incubation in 10 U/ml murine INF-γ, 5 ng/ml LPS and 39.5 mM $KNO_3$ (GLN) for 24 hours (FIG. 4). The control cells did not receive $KNO_3$. Referring to FIG. 5, the cells were activated by incubation in 10 U/ml murine INF-γ and 5 ng/ml LPS for 24 hours. Subsequently medium was removed and replaced with fresh medium (control) or medium containing 39.5 mM $KNO_3$ (GLN) for 24 hours. Referring to FIG. 6, the cells were activated by incubation in 10 U/ml murine INF-γ and 5 ng/ml LPS for 48 hours. Subsequently medium was removed and replaced with fresh medium (control) or medium containing 39.5 mM $KNO_3$ (GLN) for 24 hours. In each case, 100 μl of supernatant was removed and 10 μl DAN added and mixed. After 10 min incubation at 20° C. in the dark, the reaction was terminated with 5 μl of 2.8 N NaOH.

Fluorescence was read with excitation at 365 nm and emission read at 450 nm using a Dynatech Microfluor plate reader in white opaque 96-well plates. A standard curve using sodium nitrite was determined and used to convert fluorescence values into nitrite concentrations. The results demonstrate the increased ability of the transformed cells to convert nitrate to nitrite.

These cells can be exposed to microwave radiation in culture or when transplanted into compatible mice, with or without DALM, to measure tumor cell (growth and metabolic responses for non-ionizing radiation studies. Thus, the modified cells can be used to study mechanisms for radiofrequency and light radiation interactions with breast tumor cells in vitro and in mice. The effects of drugs, hormones, and cytokines that affect the expression of nitric oxide synthase and its activity can also be studied to understand the effects of these materials on breast tumor cells.

Various modifications may be made to the invention as described without departing from the spirit of the invention or the scope of the appended claims.

We claim:

1. The cell line EMT-6/$pSV_2neoNR10_1$.

* * * * *